United States Patent [19]
Johnstone

[11] Patent Number: 6,135,975
[45] Date of Patent: Oct. 24, 2000

[54] SURGICAL CHEST DRESSING

[75] Inventor: Haidee Johnstone, Minneapolis, Minn.

[73] Assignee: Leading Lady, Inc., Beachwood, Ohio

[21] Appl. No.: 09/241,113

[22] Filed: Feb. 1, 1999

[51] Int. Cl.[7] ................................................. A61F 13/00
[52] U.S. Cl. ........................... 602/79; 602/61; 602/19; 602/58
[58] Field of Search ................................. 602/79, 61, 19, 602/58; 450/1, 63

[56] References Cited

U.S. PATENT DOCUMENTS

| | | |
|---|---|---|
| 2,443,127 | 6/1948 | Abeles . |
| 2,596,275 | 5/1952 | Muller . |
| 2,662,522 | 12/1953 | Muller . |
| 2,800,902 | 7/1957 | Wiltrout . |
| 2,890,702 | 6/1959 | Farino . |
| 3,001,526 | 9/1961 | Krieger . |
| 3,399,669 | 9/1968 | Kaplan . |
| 3,486,501 | 12/1969 | Erickson et al. . |
| 3,561,442 | 2/1971 | Goswitz . |
| 3,568,681 | 3/1971 | Comollo . |
| 3,628,539 | 12/1971 | Fredricks . |
| 3,957,057 | 5/1976 | Farino . |
| 3,968,803 | 7/1976 | Hyman . |
| 4,314,569 | 2/1982 | Speno . |
| 4,369,792 | 1/1983 | Miller . |
| 4,475,543 | 10/1984 | Brooks et al. . |
| 5,098,331 | 3/1992 | Carrado . |
| 5,152,741 | 10/1992 | Farnio . |
| 5,188,585 | 2/1993 | Peters . |
| 5,538,502 | 7/1996 | Johnstone . |

FOREIGN PATENT DOCUMENTS

| | | |
|---|---|---|
| 1156910 | 5/1958 | France . |
| 2279344 | 2/1976 | France . |
| 597485 | 1/1948 | United Kingdom . |
| 674354 | 6/1952 | United Kingdom . |

*Primary Examiner*—Michael A. Brown
*Assistant Examiner*—Lalita Hamilton
*Attorney, Agent, or Firm*—Vickers, Daniels & Young

[57] ABSTRACT

A surgical chest dressing is constructed of a band of stretchable material having a pair of panels of non-stretchable material attached thereto, the non-stretchable panels biasing the side and breast tissue of a patient inwardly toward a sutured incision in the center of a patient's chest to support and substantially immobilize the patient's side and breast tissue and to minimize stress on the sutured incision. The dressing has a flexible and breathable back panel. The dressing provides improved support and comfort.

58 Claims, 4 Drawing Sheets

SURGICAL CHEST DRESSING

The subject invention is directed toward a surgical chest dressing and more particularly to a surgical chest dressing for minimizing stress on post-operative incisions.

INCORPORATION BY REFERENCE

U.S. Pat. No. 5,538,502 to Johnstone is incorporated by reference herein.

BACKGROUND OF THE INVENTION

After a chest operation such as open heart surgery, a patient is normally bandaged with an absorbent material over an incision and wrapped with an elastic band or dressing of the type disclosed in U.S. Pat. No. 3,968,803 to Hyman or a stretchable chest dressing of the type described in U.S. Pat. No. 5,152,741 to Farnio and U.S. Pat. No. 5,538,502 to Johnstone. Hyman, Farnio and Johnstone are all owned by a common assignee with this application and the disclosures of each are incorporated herein by reference.

Open heart surgery or other surgery where the chest cavity is opened involves making an incision over the sternum or breastbone beginning near the patient's throat and extending downwardly six to ten inches through the skin and the pectoral muscles which are attached to the sternum. Next, the ligaments which hold the ribs to the sternum must be severed so that the ribs over the patient's heart can be pried back to expose the heart and lungs. The surgery is extremely painful, and ribs, sternum and muscles must be adequately supported after surgery to allow the region to heal. The healing process may be complicated if the individual is obese and/or if a woman has large breasts. This is because the breasts or excess fatty tissue of a patient lying in a supine position tends to fall away from the center of the patient's chest and toward the sides of the patient. This, in turn, causes stress on the sutures along the sternum and causes pain as the moving flesh pulls at the injured ribs of the patient. Thus, recovery for such patients may be more painful and lengthy than it would if the breasts, breast tissue and area adjacent to the breasts were immobilized.

In the past, rigid splints were used to provide support for the chest tissue and, generally, to immobilize the chest area while the incision healed. Such splints caused breathing difficulties, were uncomfortable and therefore unacceptable. An improved dressing is disclosed in U.S. Pat. No. 5,152,741 to Farnio. The improved dressing is designed to provide support for injured tissue on the side of a patient's body which is present after a mastectomy. Such dressings may be used after any type of chest surgery, but are not well suited for relieving the stress on incisions which result from open chest surgery and the like, because they do not adequately restrain the breasts and breast tissue. If applied exceptionally tightly in an attempt to reduce the mobility of the breast tissue, flesh tends to bunch beneath the patient's arms and the patient's breasts are unduly flattened. A dressing worn in this fashion can be uncomfortable and unacceptable to the patient.

A further improvement to dressings is disclosed in U.S. Pat. No. 5,538,502 to Johnstone. This improvement is designed to form of a chest encircling flexible band of stretchable material having two substantially non-stretchable portions which conform generally to the body of the patient while the non-stretchable portions position the breasts of the patient so as reduce the stress on the incision. The chest encircling flexible band allows the dressing to expand as the patient breathes while maintaining a constant closing pressure on the incision. The elastic band is positioned at the back of the patient to be positioned away from the incision and the substantially non-stretchable pieces of material are located in proximity to the breasts of the patient when the dressing is in place. Such a dressing design overcame the problems associated with elastic material being located near the incision.

Although U.S. Pat. No. 5,538,502 to Johnstone overcame many of the problems associated with past dressings, a need still remains to provide a dressing with improved comfort to the patient.

SUMMARY OF THE INVENTION

The present invention is an improvement of dressings of the type disclosed in U.S. Pat. No. 5,538,502 to Johnstone. The dressing is a surgical chest dressing designed to improved support for a patient by holding the breasts of the patient relatively immobile while pressing them slightly toward the line of the incision and providing improved comfort during use.

In accordance with the invention, a surgical chest dressing is formed of a chest encircling flexible band of stretchable material having two substantially non-stretchable portions included therein and two free ends which are attachable to one another. The stretchable portions conform generally to the wearer's body while the non-stretchable portions position the patient's breasts so as not to stress an incision centrally located there between. In one preferred embodiment, the chest encircling flexible band is made from one or preferably two plies of stretchable material. This band may be continuous or include a panel of elastic material in the middle thereof to allow individuals of different sizes to use a particular size dressing. This elastic panel also allows the dressing to expand as the patient breathes while maintaining a constant closing pressure on the incision. In another preferred embodiment, the chest encircling flexible band includes at least two positioning stays attached to or between the plies of stretchable material to prevent the bunching of the flexible band about the body of the patient. In yet another preferred embodiment, the two panels of flexible, substantially non-stretchable pieces of material are located in proximity to the breasts of the patient when the dressing is in place. The substantially non-stretchable pieces of material are preferably designed to provide both support to the breasts of the patient and to move the breast toward one another so as to reduce the stress on the incision between the breasts. In still another preferred embodiment, the ends of the band may be attached to one another using any suitable fastener arrangement. Preferably the fastener arrangement allows the patient to easily apply, remove and adjust the dressing. One such fastener assembly is a hook and lock assembly such as a Velcro fastener assembly.

In accordance with yet another aspect of the present invention, the chest encircling flexible band includes a section of highly breathable material. The highly breathable material is designed to provide aeration of the dressing when on the patient to reduce the heat and moisture buildup when the dressing is used by the patient. The highly breathable material is preferably a flexible material which may be stretchable or nonstretchable. The highly breathable material is preferably located at the back of the patient when the dressing is in place.

In accordance with another aspect of the present invention, the chest encircling flexible band includes a section of flexible material to increase the comfort to the patient when the dressing is in place. The flexible material allows for slight adjustments of the dressing on the back of the patient to improve the comfort of the dressing.

In accordance with still another aspect of the present invention, the dressing includes straps to provide improved adjustment of the dressing, provide additional flexibility in the dressing to allow the patient to easily breathe, and to provide additional support to the breasts of the patient. The straps can include non-stretchable and stretchable components. In one preferred embodiment, the strap includes a stretchable portion and a non-stretchable portion.

It is therefore a principal object of the present invention to provide a surgical chest dressing for patients who have undergone chest surgery.

It is another object of the present invention to provide a surgical chest dressing which is comfortable to wear.

It is a further object of the present invention to provide a surgical chest dressing which minimizes stress on surgical incisions.

It is another object of the present invention to provide a chest dressing which maintains an even closing pressure across the incision along the entire length of the incision.

It is still a further object of the present invention to provide a chest dressing which does not fold and bunch uncomfortably beneath the wearer's arms.

It is yet another object of the present invention to provide a surgical chest dressing which substantially immobilizes the breasts of the wearer.

It is yet a further object of the present invention to provide a surgical chest dressing which is acceptable to both male and female patients.

It is still another object of the present invention to provide a surgical chest dressing which immobilizes the breasts of the wearer without causing excess flesh beneath the wearer's arms to bulge out.

It is still a further object of the present invention to provide a surgical chest dressing made from stretchable material which allows a patient to cough and breathe deeply without stressing an incision in the patient's chest.

It is yet another object of the present invention to provide a surgical chest dressing for biasing the breast tissue of a person away from a person's sides and the tissue adjacent a person's armpit toward the person's front.

It is still yet another object of the present invention to provide a surgical chest dressing that is easily adjustable.

It is another object of the present invention to provide a surgical chest dressing that reduces moisture buildup.

It is yet another object of the present invention to provide a surgical chest dressing that provides improves air circulation of the dressing when worn by the patient.

These and other objects and advantages will become apparent to those skilled in the art upon reading the following description taken together with the accompanying drawings.

DETAILED DESCRIPTION OF PREFERRED EMBODIMENTS

Figure 1:
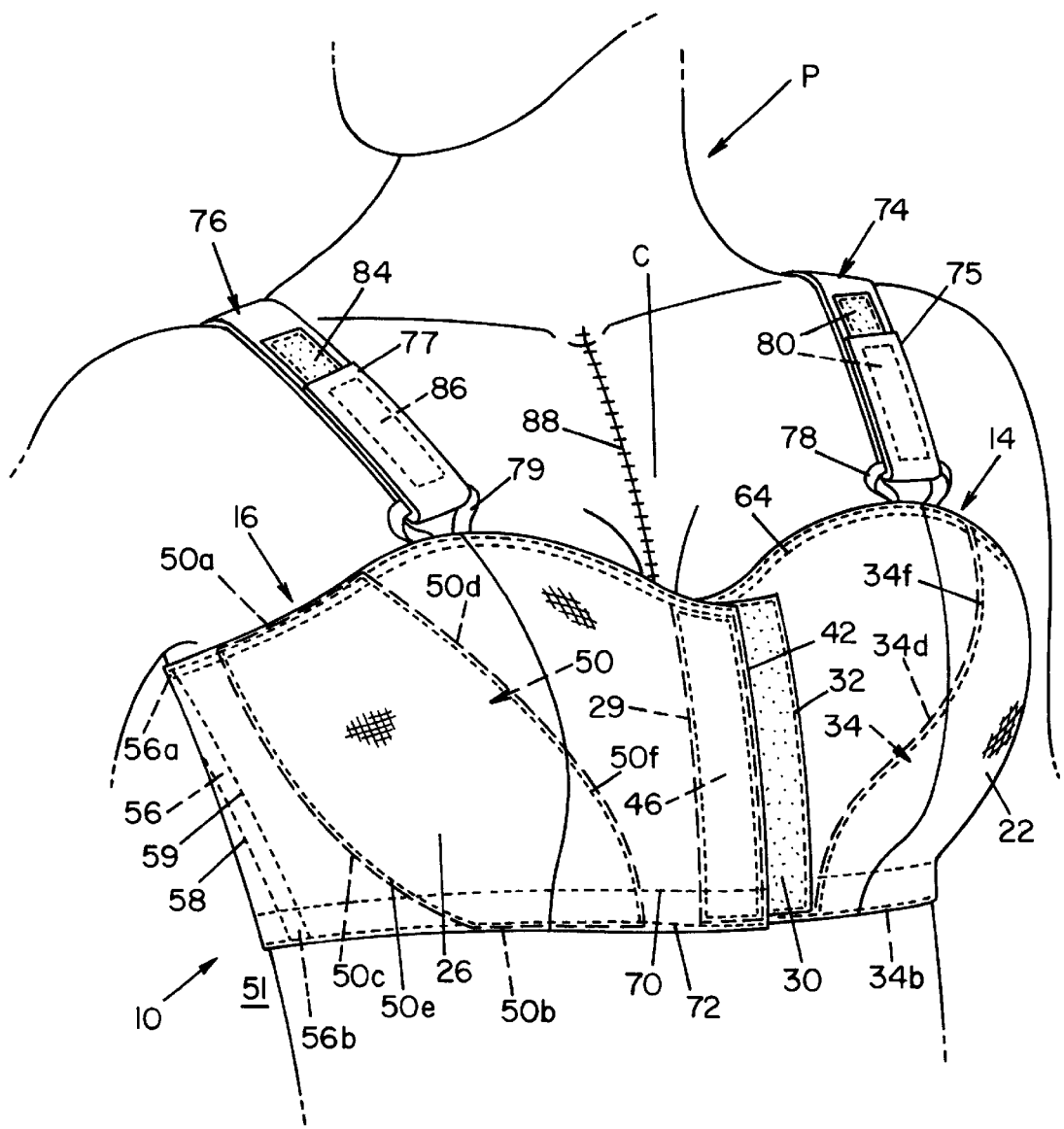
FIG. 1 is a perspective view showing a patient wearing a surgical chest dressing in accordance with the invention and which dressing includes optional shoulder straps.
Figure 2:
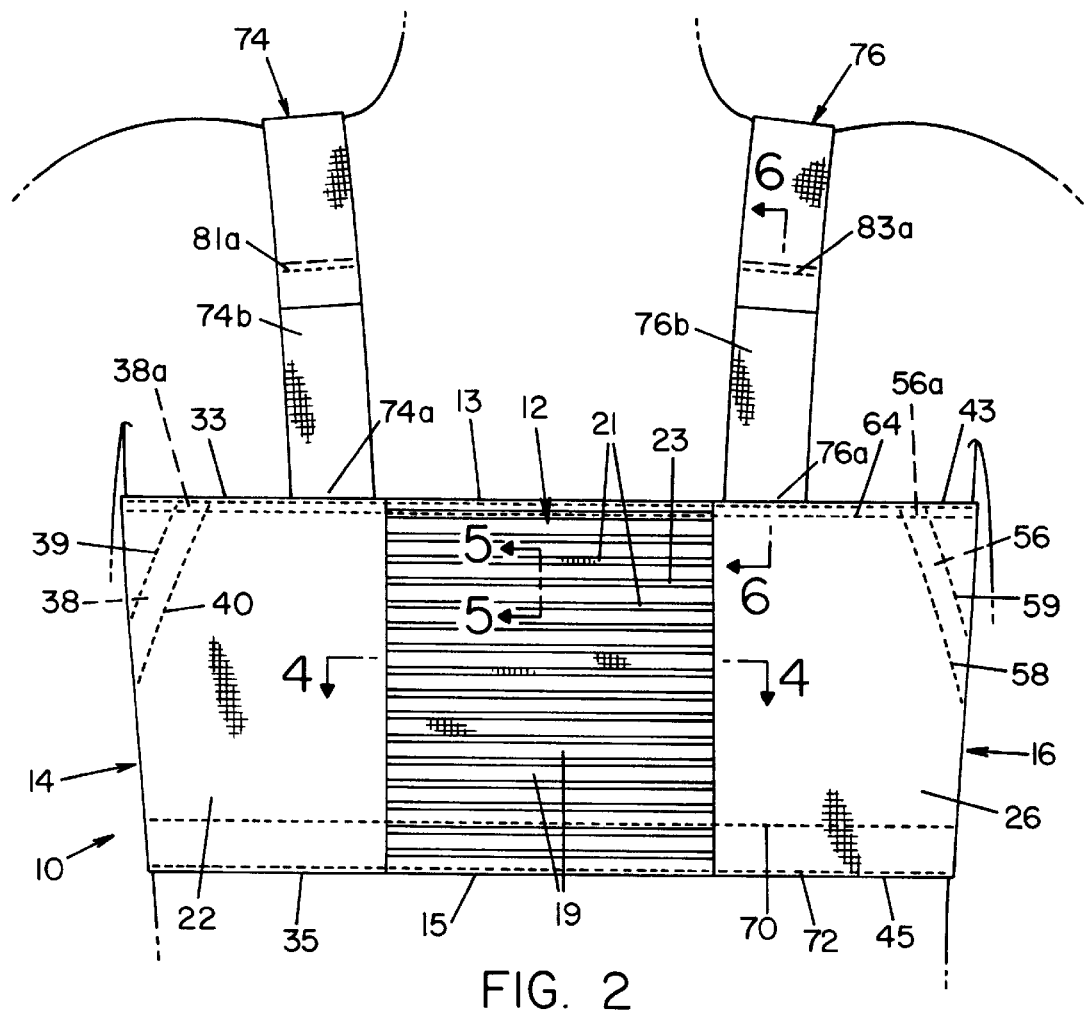
FIG. 2 is a rear view showing the back of the surgical chest dressing of FIG. 1.
Figure 3:
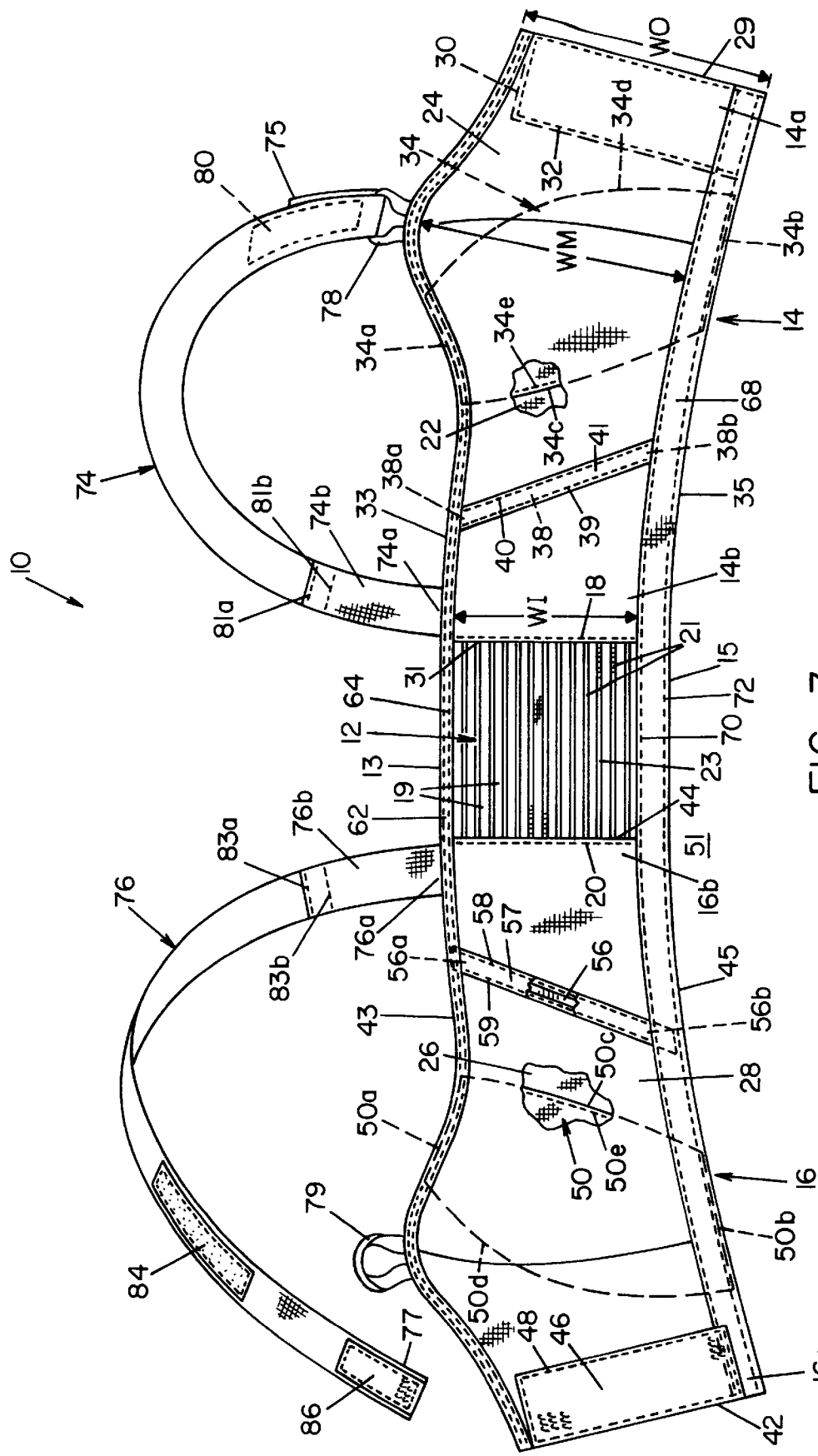
FIG. 3 is a perspective view of the inside of the surgical chest dressing in accordance with the invention.

Referring now to the drawings wherein the showings are for the purpose of illustrating preferred embodiments of the invention only and not for the purpose of limiting same, FIG. 1 illustrates a surgical chest dressing 10 wrapped around the chest region C of a person P. As shown in FIGS. 2 and 3, dressing 10 comprises an elastic central panel 12 having a top edge 13 and a bottom edge 15 joined to a left dressing half 14 by stitching 18 and to a right dressing half 16 by stitching 20. As can be appreciated, other joining arrangements may be used to secure left dressing half 14 and/or right dressing half 16 to central panel 12.

Figure 4:
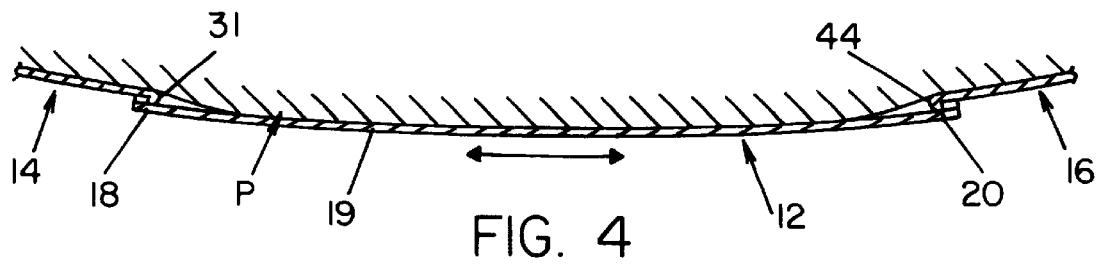
FIG. 4 is a cross-sectional view taken through line 4—4 in FIG. 2.
Figure 5:
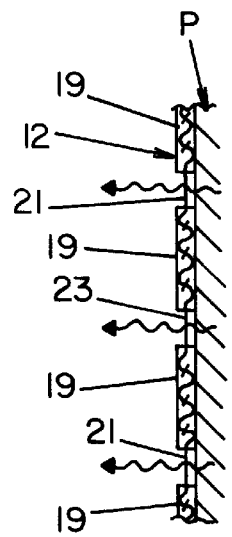
FIG. 5 is a cross-sectional view taken through lines 5—5 in FIG. 2.
Figure 6:
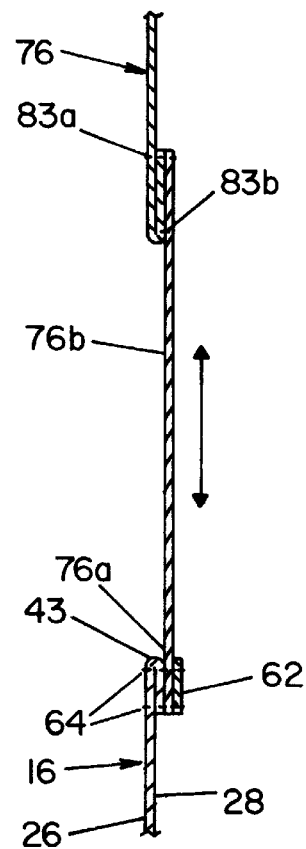
FIG. 6 is a cross-sectional plan view taken through line 6—6 in FIG. 2.

Referring specifically to FIGS. 4 and 5, central panel 12 includes several longitudinally extending elastic bands 19 that are spaced apart and which are connected together by spaced threads 21. Threads 21 preferably run the complete lateral length of central band 12. Positioned between every other band is a band of woven and/or unwoven fibers 23. Elastic bands 19 allow the central panel to be stretched along the longitudinal length of the panel. Threads 21 are preferably not elastic thereby preventing central panel 12 from being stretched in the lateral direction. As can be appreciated, the central panel can be designed to not stretch or stretch in the longitudinal and/or lateral direction. In addition, fibers 23 may be positioned on more or less of threads 21 or may be completely eliminated. Central panel 12 is designed to allow dressing 10 to stretch so as to increase the flexibility and comfort of the dressing on the wearer. Central panel 12 is also designed to aerate so as to reduce the heat buildup on the patient and to reduce the amount of moisture buildup between the dressing and the patient. The amount of spacing between threads 21 can be varied to obtain the desired amount of aeration, comfort and flexibility provided by the central panel. In addition, the amount and density of fibers 23 can be varied to affect the amount of aeration, comfort and flexibility by the central panel. The elastic bands 19 may be designed to be more or less dense thereby also affecting the amount of aeration, comfort and flexibility of the central panel. Preferably the central panel is made of elastic and nylon.

Referring now to FIGS. 1 and 3, left panel half 14 includes an outer end 14a having an outer edge 29, an inner end 14b having an inner edge 31, a top edge 33 and a bottom edge 35. Right dressing half 16 includes an outer end 16a having an outer edge 42, an inner end 16b having an inner edge 44, a top edge 43 and a bottom edge 45. The terms "left" and "right" are used to describe the orientation of dressing halves 14, 16 as shown in FIG. 3. When dressing 10 is placed on a patient, left dressing half 14 will overlay the left side of the patient's chest and right dressing half 16 will overlay the right side of a patient's chest; however, a person looking from the front at a person wearing dressing 10, as in FIG. 1, will see these directions as reversed. Left dressing half 14 and right dressing half 16 are substantially identical to one another except with respect to the fasteners used on the respective halves which will be described in greater detail hereinafter. Left dressing half 14 comprises. two plies of a stretchable material, an outer ply 22 and an inner ply 24, and right dressing half 16 comprises an outer ply 26 and an inner ply 28. As can be appreciated, the left dressing half 14 and/or right dressing half 16 may include more or less plies. The material of plies 22, 24 26 and 28 may, for example, be 100% nylon jersey.

Working from the outer edge 29 of left dressing half 14 toward inner edge 31 of left dressing half 14, dressing half 14 comprises a panel 30 of the loop component of a hook and loop fastener which is attached to plies 22 and 24 by stitching 32 such that the loop fastener on panel 30 will face away from chest region C of a patient wearing dressing 10. Moving away from outer edge 29, left dressing half 14 next comprises a panel 34 of non-stretchable material is disposed between outer ply 22 and inner ply 24 and fastened between plies 22 and 24, as explained more fully hereinafter. Panel 34 is preferably a flexible material such as latex foam covered with acetate tricot. Moving away from inward edge 34c of panel 34, left dressing half 14 next comprises a stay 38 secured to left dressing half 14 by stay cover 41. Stay cover 41 overlies inner ply 24 and is attached to plies 22 and 24 by stitching 39 and 40 to hold a stay 38 between stay cover 41 and inner ply 24. As can be appreciated, other manners of fastening may be used. In addition, stay 38 may be positioned between plies 22 and 24 or overlie outer ply 22. Stay 38 is preferably formed from a durable flexible material such as a thin metal or plastic strip.

Working from outer end 42 of right dressing half 16 toward inner edge 44 of right dressing half 16, dressing half 16 comprises a panel 46 of the hook component of a hook and loop fastener fastened to plies 26 and 28 by stitching 48 such that the hooks on panel 46 face toward the chest region C of a patient wearing dressing 10. Moving away from outer edge 42, right dressing half 16 next comprises a panel 50 of the same non-stretchable material as panel 34 disposed between outer ply 26 and inner ply 28 and fastened between plies 26 and 28 as described hereinafter. Moving away from inward edge 50c of panel 50, right dressing half 16 next comprises a stay 56 secured to right 25 dressing half 16 by stay cover 57. Stay cover 57 overlies inner ply inner ply 28 and is attached to plies 26 and 28 by stitching 58 and 59 to hold a stay 56 between stay cover 57 and inner ply 28. As can be appreciated, other manners of fastening stay 56 may be used. In addition, stay 56 may be positioned between plies 26 and 28 or overlie outer ply 26.

Referring now to FIG. 3, the stitching panel 50 and stay cover 57 on panel half 16 is shown. Edges 50a–d are stitched to outer ply 26 thereby securing panel 50 in place with respect to outer ply 26. By connecting panel 50 to outer ply 26, inner ply which is contact with the breast of the patient can slightly adjust independently of panel 50 and outer ply 26 thus providing greater comfort during breathing without sacrificing support of the breast. As can be appreciated, panel 50 may alternatively be connected to inner ply 28 or to both plies 26 and 28. Stay cover 57 is stitched to both plies 26 and 28 to prevent the bunching of both plies. As can be appreciated, stay cover 57 may alternatively be connected to a single ply.

Referring now to FIGS. 1 and 3, left dressing half 14 has an outer width WO along outer edge 29, an inner width WI along inner edge 31, and a maximum width WM located approximately one-third of the distance inwardly from outer edge 29. Width WO is preferably about the same or greater than width WI. Bottom edge 35 of left dressing half 14 is substantially straight or slightly concave between outer edge 29 and inner edge 31. The width of dressing 10 across left dressing half 14 increases inwardly from outer edge 29 as top edge 33 of dressing half 14 curves away from bottom edge 35 of dressing half 14 until the maximum width WM is reached at a point approximately one-third of the way in from edge 29. From the point at which width WM is reached, top edge 33 slopes back toward bottom edge 35 and the width of dressing 10 decreases between width WM and width WI. In the region about width WM, inner and outer plies 22 and 24 form a cup to receive a portion of a patients breast and to support such breast. The size of the cup may be varied to accommodate different breast sizes to as to increase the comfort to the patient and provide the desired support and positioning of the patient's breast. In addition, the width of left dressing half 14 between WO and WM and between WM and WI is selected to cover, support and position the top portion of the patient's breast. Width WM can be varied to accommodate different breast sizes of a patient. Left panel half 14 and right panel half 16 are substantially mirror images of each other except for the different fastener components 30 and 46. The section of top edge 33 and bottom edge 35 near edge 29 of left panel half 14 are closely parallel to one another. Similarly, the section of top edge 43 and bottom edge 45 near edge 42 of right panel half 16 are closely parallel to one another. This design of the sections of band 10 near edges 29 and 42 facilitate in the ease of connecting the edges together and provides the desired support of band 10 along the longitudinal length the band 10.

Referring now to FIGS. 1, 2 and 3, a top strip of elastic material 62 runs from outer edge 29 of left dressing half 14 across top edge 33 of dressing half 14, across top edge 13 of central panel 12, across top edge 43 of right dressing half 16 and terminates at outer edge 42 of dressing half 16. The top elastic strip is shown fastened in place by two rows of zig zag stitching 64, 66; however, the elastic strip can be fastened by a single row of stitching or more than two rows of stitching, stitching having other designs, and/or other well known attachment methods could also be used. In a similar manner, a bottom elastic strip 68 runs from outer edge 29 of left dressing half 14 across bottom edge 35 of dressing half 14, across the bottom edge 15 of central panel 12, across bottom edge 45 of right panel half 16 and terminates at outer edge 42 of dressing half 16. Bottom strip 68 is shown fastened in place by stitching 70 and 72 but a single row of zig zag stitching or other well known attachment method could also be used. Elastic strips 62 and 68 are designed to position the band 10 securely against the body of person P.

The interior surface of elastic material 62 and 68 includes a plush surface to increase the comfort to the wearer. The plush surface is formed of a soft, non-woven material; however, other soft materials can be used.

Referring now to FIGS. 1 and 3, panel 34 of non-stretchable material is defined by a top 20 edge 34a, a bottom edge 34b an inner edge 34c, and an outer edge 34d. The shape of panel 34 is selected to provide the desired support and positioning of the patient's breast. Top edge 34a is positioned adjacent to and generally coincides with the corresponding portion of top edge 33 of left dressing half 14 in the region between width WM to width WI. Similarly, bottom edge 34b of panel 34 positioned adjacent to and generally coincides with the corresponding portion of bottom edge 35 of dressing half 14. Outer edge 34d is preferably has a greater degree of curvature than inner edge 34c. As shown in FIGS. 3, inner edge 34 is nonparallel with inner edge 31 of central panel dressing hall 14 and is preferably substantially straight, thus having little or no curvature. Similarly, panel 50 of non-stretchable material is defined by a top edge 50a, a bottom edge 50b an inner edge 50c, and an outer edge 50d. The shape and positioning of panel 50 on right dressing half 16 is substantially a mirror image of panel 34 on left dressing half 14.

As illustrated in FIGS. 1,2 and 3, on the left dressing half 14, stay 38 is located between panel 34 and inner edge 31 and extends between top edge 33 and bottom edge 35 of left dressing half 14. Stay 38 is secured at its top end 38a by stitching 66 and at its bottom end 38b by stitching 70. Inner edge 34c of panel 34 is secured to outer ply 26 by a row of stitching 34e and outer edge 34d of panel 34 is secured to outer ply 26 by a row of stitching 34f. Top edge 34a of panel 34 is held in place by stitching 64 which runs along top elastic strip 62. Bottom edge 34b of panel 34 is held in place and secured to inner and outer plies 26 by stitching 70 and 72, which stitching also secures bottom elastic strip 68 to dressing 10. On right dressing half 16, stay 56 is located between panel 50 and inner edge 44 and extends between top edge 43 and bottom edge 45 of right dressing half 16. Stay 56 is secured at its top end 56a by stitching 64 and at its bottom end 56b by stitching 70. Inner edge 50c of panel 50 is secured to outer ply 26 by a row of stitching 50e and outer edge 50d of panel 50 is secured to outer ply 26 by a row of stitching 50f. Top edge 50a of panel 50 is held in place by stitching 64 which runs along top elastic strip 62. Bottom edge 50b of panel 50 is held in place and secured to inner and outer plies 24 and 26 by stitching 70 and 72, which stitching also secures bottom elastic strip 68 to dressing 10.

Shoulder straps or supports are preferably used to provide additional support. As can be appreciated, the shoulder straps can be eliminated if additional support is not needed and/or if not desired. As best illustrated in FIG. 1,2,3 and 6, a left elastic section 74b is attached to left dressing half 14 and a right elastic section 76b is attached to right dressing half 16. End 74a of elastic section 74b is attached to top edge 33 of left dressing half 14 between plies 22 and 24 and elastic strip 62 by stitching 64. End 74a is secured to left dressing half 14 between inner edge 31 and stay 38. A loop 78 is attached to top edge 33 of left dressing half 14 between outer edge 34d of panel 34 and outer edge 29, and preferably in the general vicinity of the maximum width WM thereof. Loop 78 is held in place between plies 22 and 24 and elastic strip 62 by stitching 64. Strap 74 has an end 75 and panels of a hook and loop fastener are affixed to strap 74 on one side of end 75 as designated generally by numeral 80 and which panels are comparable to adjustably attach end 75 to loop 78. Strap 74 is connected to elastic section 74b. Elastic section 74b is secured to strap 74 by stitching 81a and 81b. Similarly, end 76a of elastic section 76b is attached to top edge 43 of right dressing half 16 between plies 24 and 26 and elastic strip 62 by stitching 64. End 76a is secured to right dressing half 16 between inner edge 44 and stay 56. A loop 79 is attached to top edge 43 of right dressing half 16 between outer edge 50d of panel 50 and outer edge 42, and preferably in the general vicinity of the maximum width WM thereof. Loop 79 is held in place between plies 26 and 28 and elastic strip 62 by stitching 64. Strap 76 has an end 77 and panels of a hook and loop fasteners 84 and 86 affixed to strap 76 on one side of end 77 for adjustably attaching end 77 to loop 79. Strap 76 is connected to elastic section 76b to allow strap 76. Elastic section 76b is secured to strap 76 by stitching 83a and 83b.

To apply dressing 10 to a patient, as best seen in FIGS. 1–3, dressing 10 is laid flat on a horizontal surface 51, such as a bed, with inner plies 24 and 28 facing away from surface 51. A patient P is placed on dressing 10 in a supine position so that central panel 12 is generally centered from left to right across the patient's back and below the post-operative incision. In this position, outer edge 42 and part of right dressing half 16 will extend outwardly of the patient's right side and outer edge 29 and a portion of left dressing half 14 will extend outwardly of the patient's left side. If the dressing has the optional shoulder straps, the straps are positioned so that left strap 74 extends upwardly from beneath the patient's left shoulder next to the left side of the patient's head and the right shoulder strap 76 extends upwardly from beneath the patient's right shoulder next to the right side of the patient's head. Left and right dressing halves 14 and 16 and hook and loop panels 30 and 46 thereof are brought beneath the patient's arms and across the patient's chest toward each other and toward incision 88. Panels 46 and 30 are pulled into an overlapping position and pressed together to fasten dressing 10 snugly about the patient's chest. If the dressing has shoulder straps, at this time left strap 74 is pulled over the patient's left shoulder, end 75 is inserted through loop 78, pulled snug, and folded over so that the hook and loop fastener 80 will hold the strap in position. Right strap 76 is positioned and fastened in a similar manner by hook and loop components 84 and 86. FIG. 1 shows dressing 10 having shoulder straps fastened in this manner.

The dressing provides adequate lateral support to keep the breasts of a patient in a supine position thus preventing the breasts to fall toward the sides of the patient's body and thus reducing stress on incision 88. This stress is not only painful for the patient but also can slow down the healing process with respect to incision 88 and can result in the incision not healing properly.

The dressing 10 advantageously biases the sides and breasts of the patient inwardly toward incision 88 to prevent incision 88 from being stressed. More particularly in this respect, in fastening left dressing half 14 to right dressing half 16, left dressing half 14 is first pulled between the patient's left arm and left side so that it is generally perpendicular to central panel 12, and right dressing half 16 is similarly oriented so that it is parallel to left dressing half 14. The right and left halves are then pulled across the patient's chest toward incision 88 and are fastened together by hook and loop components 30 and 46. FIGS. 1 and 2 illustrate the panels 34 and 50 positioned along the corresponding side of the patient including the outer sides of the patient's breasts. In these positions of panels 34 and 50, the top, bottom, outer and inner edges thereof are positioned relative to the patient's body. Referring specifically to FIG. 1, top edge 50a of panel 50 extends along the patient's side and the upper area of the breast toward the patient's front while outer edge 50c extends along the side of the breast from top edge 50a to bottom elastic strip 68 and bottom edge 50b of the panel. Elastic strip 68 and the bottom edge portion of panel 50 are positioned beneath the breast and preferably extend inwardly a short distance there beneath. As will be further appreciated, outer edge 50d of panel 50 extends laterally outwardly and generally across the center of the patient's breast from bottom edge 50b to top edge 50a. As can be appreciated, panel 34 is oriented similarly to panel 50.

During pulling of dressing halves 14 and 16 across the chest to engage hook and loop fastener components 30 and 46, the corners of panels 34 and 50 formed by the top and outer edges thereof compress the patient's flesh in the area near the corresponding armpit toward the patient's front to prevent any uncomfortable rubbing or chafing. As dressing halves 14 and 16 are pulled toward the patient's front, panels 34 and 50 engage the outerside and underside of the corresponding breast to support and push it toward incision 88. As will be further appreciated, the shape of nonstretchable panels 34 and 50 allows the panels to provide the greatest amount of support and bias for the patient's breasts without constricting other parts of a patient's back, breasts or sides. When dressing 10 is properly positioned, inner edges 34c and 50c of panels 34 and 50 slope downwardly and inwardly from the patient's armpit areas to prevent any uncomfortable restriction of the patient's flesh on the patient's sides. Inner edges 34c and 50c begin near the location where the patient's corresponding arm meets the patient's front and extends downwardly and inwardly toward incision 88 to bottom elastic strip 68. Being so shaped, non-stretchable panels 34 and 50 lift and bias the patient's breasts away from the patient's sides while the stretchable material in other areas of the right and left dressing halves where less support is needed provides for maximum comfort. This differential support both speeds healing and maximizes comfort.

As will be appreciated from FIGS. 1 and 2 stays 38 and 56 are located along the sides of the patient beneath the patient's armpits. These stays help to support the portions of dressing 10 along the patient's sides and to keep dressing 10 flat against the patient's body. Without these stays, dressing 10 could roll or bunch beneath the patient's arms. Such bunching is not only uncomfortable, but also alters the tension placed on incision 88 by dressing 10. If dressing 10 is too tight across some portions of incision 88 and not tight enough across others, unnecessary stresses will be placed on the incision, interfering with the healing process. By keeping dressing 10 flat against the patient's body, stays 38 and 56 help maintain an even pressure across the patient's chest and across incision 88 therein. Stays 38 and 56 are positioned across the width of dressing 10 so that end 38a of stay 38 is closer to central panel 12 than is end 38b of stay 38 and such that end 56a of stay 56 is positioned closer to stay 56 than is end 56b. In addition, stay 38 is substantially parallel to inward edge 34c of panel 34, and stay 56 is substantially parallel to inward edge 50c of panel 50. In this manner, as best seen with respect to stay 56 in FIG. 1, when dressing 10 is placed on a patient, end 56a is closer to horizontal surface 51 than is end 56b. By angling the stay 38 and 56, the stays do not poke or jab a patient in the side. By angling the stays so that ends 38b and 56b are closer to the patient's chest, the stays tend to slide against the patient's side as the patient breathes, instead of poking or jabbing the patient. In the preferred embodiment, ends 38a and 56a are offset about 0.5 to 2.5 inches from ends 38b and 56b, respectively.

The invention has been described with reference to preferred embodiments and it is apparent that other embodiments, as well as modifications of the preferred embodiments can be made without departing from the principles of the invention. Accordingly, it will be distinctly understood that the foregoing descriptive matter is to be interpreted merely as illustrative of the invention and not as a limitation.

Having thus described the invention, it is claimed:

1. A surgical chest dressing comprising:
   a chest encircling flexible band formed primarily from a stretchable material and having free ends overlapping each other at engaging surfaces generally centrally of the chest of a person about which the dressing has been wrapped; and
   said band including first and second non-stretchable support panels and a flexible aeration panel, said support panels biasing body tissue of said person there between in a desired direction relative to the person's chest, said flexible aeration panel positioned at least partially between said support panels and at least partiality positionable on the back of said person when said band is secured to said person, wherein said flexible aeration panel includes a stretchable material and a plurality of low air resistant sections, said low air resistant sections providing for greater air flow therethrough than said support panels.

2. A surgical chest dressing as defined in claim 1, wherein said first and second non-stretchable support panels are separated by a first section of stretchable material and spaced apart from each of said free ends by second sections of stretchable material.

3. A surgical chest dressing as defined in claim 1, wherein said first non-stretchable support panel overlies a portion of at least one side of said person's breast.

4. A surgical chest dressing as defined in claim 1, wherein said second non-stretchable support panel overlies a portion of at least one side of said person's breast.

5. A surgical chest dressing as defined in claim 4, wherein said first non-stretchable support panel overlies at least one side of said breast on one side of the person's chest and said second non-stretchable support panel overlies at least one side of said breast on the opposite side of the person's chest.

6. A surgical chest dressing as defined in claim 1, wherein said flexible aeration panel positioned between said first and second non-stretchable support panel.

7. A surgical chest dressing as defined in claim 1, wherein said flexible aeration panel includes at least one low air resistant section positioned substantially across the longitudinal length of said panel.

8. A surgical chest dressing as defined in claim 1, including at least one stiffener to reduce transverse folding of said band to the direction between said free ends along said person's sides.

9. A surgical chest dressing as defined in claim 8, wherein said at least one stiffener includes a strip member of flexible material attached to said band.

10. A surgical chest dressing as defined in claim 9, wherein said strip member positioned substantially parallel to an adjacent side of at least one of said non-stretchable support panels.

11. A surgical chest dressing as defined in claim 1, wherein said band means includes upper and lower edges between said ends, an upper band of elastic material attached to an upper edge, and a lower band of elastic material attached to a lower edge.

12. A chest encircling dressing comprising band means of stretchable material having free ends, at least two panels of non-stretchable material attached to said band means to bias the breast tissue of a person wearing said dressing inwardly of said person's chest, at least one of said non-stretchable panels being separated by at least one section of stretchable material, at least one of said non-stretchable panels being separated from at least one of said free ends by at least one section of stretchable material, and at least one stiffener to reduce transverse folding of said band to the direction between said free ends along said person's sides, said at least one stiffener positioned substantially parallel to an adjacent side of at least one of said non-stretchable support panels, said stiffener including a material different from said non-stretchable panels, said at least one stiffener includes a strip member of flexible material attached to said band, said band means includes upper and lower edges between said ends, said stiffener extending between and substantially to said upper and lower edges of said band.

13. A chest dressing as defined in claim 12, wherein said band means comprises two plies of stretchable material fastened together, said panels of non-stretchable material being disposed there between.

14. A chest dressing as defined in claim 12, including an aeration panel positioned on said band means.

15. A chest dressing as defined in claim 14, wherein said aeration panel positioned between said at least two panels of non-stretchable material.

16. A chest dressing as defined in claim 14, wherein said aeration panel includes at least one low air resistant section positioned substantially across the longitudinal length of said panel.

17. A chest dressing as defined in claim 14, wherein said aeration panel includes a stretchable material and a plurality of low air resistant sections.

18. A chest dressing as defined in claim 17, wherein said aeration panel stretchable in a longitudinal length.

19. A chest dressing as defined in claim 18, wherein said aeration panel substantially nonstretchable in a latitudinal width.

20. A chest dressing as defined in claim 17, wherein said plurality of low air resistant sections positioned substantially along a longitudinal axis of said aeration panel.

21. A chest dressing as defined in claim 12, wherein said band means includes upper and lower edges between said ends, an upper band of elastic material attached to an upper edge, and a lower band of elastic material attached to a lower edge.

22. A chest dressing as defined in claim 12, wherein said band means includes at least two elastic straps connected to an upper edge of said band means to at least partially support said dressing on the shoulders of said person.

23. A chest dressing as defined in claim 12, wherein said stiffener includes plastic or metal.

24. A chest dressing as defined in claim 12, including an aeration panel positioned on said band means and at least partially between said at least two panels of non-stretchable material.

25. A chest dressing as defined in claim 24, wherein said aeration panel includes a plurality of low air resistant section positioned substantially across the longitudinal length of said panel.

26. A surgical chest dressing as defined in claim 25, wherein said flexible aeration panel includes a first and second fiber, said first fiber being at partially elastic, said second fiber being substantially nonelastic, said first fiber enabling said flexible aeration panel to stretch in at least one direction, said second fiber inhibiting said flexible aeration panel from stretching in at least one direction.

27. A surgical chest dressing comprising elongate band means of stretchable material having a first end and a second end, and first and second interengagable fastening means respectively on said first and second ends of said band means, said band means including spaced apart edges extending between said first and second ends, said edges providing for said band means to have a first width in a central portion of said band means between said ends and a second width between said first and second ends of said band means respectively between said central portion and said first end and between said central portion and said second end, said second width being greater than said first width, said central portion of said band means including a flexible aeration panel, a first non-stretchable panel supported on a first portion of said band means between and spaced apart from said elastic panel and said first fastening means, and a second non-stretchable panel supported on a second portion of said panel means between and spaced apart from said elastic panel and said second fastening means, said flexible aeration panel at least partially positioned on said first section of stretchable material.

28. A surgical chest dressing as defined in claim 27, wherein said first and second fastening means comprise interengaging loop and hook components.

29. A surgical chest dressing as defined in claim 28, wherein said flexible aeration panel includes a first and second fiber, said first fiber being at partially elastic, said second fiber being substantially nonelastic, said first fiber enabling said flexible aeration panel to stretch in at least one direction, said second fiber inhibiting said flexible aeration panel from stretching in at least one direction.

30. A surgical chest dressing as defined in claim 27, wherein said flexible aeration panel includes a stretchable material and a plurality of low air resistant sections positioned substantially across the longitudinal length of said panel, said aeration panel stretchable at least along said longitudinal length.

31. A surgical chest dressing as defined in claim 30, wherein said flexible aeration panel substantially nonstretchable along a latitudinal width.

32. A surgical chest dressing as defined in claim 30, including at least one stiffener to reduce transverse folding of said band to the direction between said free ends along said person's sides, said strip member positioned substantially parallel to an adjacent side of at least one of said non-stretchable support panels.

33. A surgical chest dressing as defined in claim 32, wherein said band means includes upper and lower edges between said ends, said stiffener extending between and substantially to said upper and lower edges of said band.

34. A surgical chest dressing as defined in claim 33, wherein said stiffener includes plastic or metal.

35. A surgical chest dressing as defined in claim 27, including at least one stiffener to reduce transverse folding of said band to the direction between said free ends.

36. A surgical chest dressing as defined in claim 35, wherein said at least one stiffener includes a strip member of flexible material attached to said band, said strip member positioned substantially parallel to an adjacent side of at least one of said non-stretchable panels.

37. A chest dressing as defined in claim 27, wherein said band means includes at least two elastic straps connected to an upper edge of said band means to at least partially support said dressing on the shoulders of a person.

38. A surgical chest dressing as defined in claims 27, wherein said flexible aeration panel is completely on said first section of stretchable material.

39. A surgical chest dressing comprising:
   a chest encircling flexible band formed primarily from a stretchable material and having free ends overlapping each other at engaging surfaces generally centrally of the chest of a person about which the dressing has been wrapped; and
   said band including first and second non-stretchable support panels and a flexible aeration panel, said support panels biasing body tissue of said person there between in a desired direction relative to the person's chest, said first and second non-stretchable support panels are separated by a first section of stretchable material and spaced apart from each of said free ends by second sections of stretchable material, said flexible aeration panel positioned at least partially between said support panels and at least partiality positionable on the back of said person when said band is secured to said person, said flexible aeration panel at least partially positioned on said first section of stretchable material.

40. A surgical chest dressing as defined in claims 2, wherein said flexible aeration panel is completely on said first section of stretchable material.

41. A surgical chest dressing as defined in claim 39, wherein said first non-stretchable support panel overlies at least one side of said breast on one side of the person's chest and said second non-stretchable support panel overlies at least one side of said breast on the opposite side of the person's chest.

42. A surgical chest dressing as defined in claim 41, wherein said flexible aeration panel positioned between said first and second non-stretchable support panel.

43. A surgical chest dressing as defined in claim 42, wherein said flexible aeration panel includes at least one low air resistant section positioned substantially across the longitudinal length of said panel.

44. A surgical chest dressing as defined in claim 43, wherein said flexible aeration panel includes a stretchable material and a plurality of low air resistant sections.

45. A surgical chest dressing as defined in claim 44, wherein said flexible aeration panel includes a first and second fiber, said first fiber being at partially elastic, said second fiber being substantially nonelastic, said first fiber enabling said flexible aeration panel to stretch in at least one direction, said second fiber inhibiting said flexible aeration panel from stretching in at least one direction.

46. A surgical chest dressing as defined in claim 45, wherein said flexible aeration panel includes a plurality of low air resistant sections.

47. A surgical chest dressing as defined in claim 46, including at least one stiffener to reduce transverse folding of said band to the direction between said free ends along said person's sides, said strip member positioned substantially parallel to an adjacent side of at least one of said non-stretchable support panels.

48. A surgical chest dressing as defined in claim 47, wherein said stiffener includes plastic or metal.

49. A surgical chest dressing as defined in claim 42, wherein said first and second nonstretchable support panels are separated by a first section of stretchable material and spaced apart from each of said free ends by second sections of stretchable material, said flexible aeration panel positioned at least partially between said support panels and at least partiality positionable on the back of said person when said band is secured to said person, said flexible aeration panel at least partially positioned on said first section of stretchable material.

50. A surgical chest dressing as defined in claim 49, wherein said flexible aeration panel is completely on said first section of stretchable material.

51. A surgical chest dressing as defined in claim 49, wherein said first non-stretchable support panel overlies at least one side of said breast on one side of the person's chest and said second non-stretchable support panel overlies at least one side of said breast on the opposite side of the person's chest.

52. A surgical chest dressing as defined in claim 49, wherein said flexible aeration panel positioned between said first and second non-stretchable support panel.

53. A surgical chest dressing as defined in claim 49, wherein said flexible aeration panel includes at least one low air resistant section positioned substantially across the longitudinal length of said panel.

54. A surgical chest dressing as defined in claim 49, wherein said flexible aeration panel includes a stretchable material and a plurality of low air resistant sections.

55. A surgical chest dressing as defined in claim 49, wherein said flexible aeration panel includes a first and second fiber, said first fiber being at partially elastic, said second fiber being substantially nonelastic, said first fiber enabling said flexible aeration panel to stretch in at least one direction, said second fiber inhibiting said flexible aeration panel from stretching in at least one direction.

56. A surgical chest dressing as defined in claim 49, wherein said flexible aeration panel includes a plurality of low air resistant sections.

57. A surgical chest dressing comprising:

a chest encircling flexible band formed primarily from a stretchable material and having free ends overlapping each other at engaging surfaces generally centrally of the chest of a person about which the dressing has been wrapped; and said band including first and second non-stretchable support panels and a flexible aeration panel, said support panels biasing body tissue of said person there between in a desired direction relative to the person's chest, said flexible aeration panel includes a first and second fiber, said first fiber being at partially elastic, said second fiber being substantially nonelastic, said first fiber enabling said flexible aeration panel to stretch in at least one direction, said second fiber inhibiting said flexible aeration panel from stretching in at least one direction.

58. A surgical chest dressing comprising elongate band means of stretchable material having a first end and a second end, and first and second interengagable fastening means respectively on said first and second ends of said band means, said band means including spaced apart edges extending between said first and second ends, said edges providing for said band means to have a first width in a central portion of said band means between said ends and a second width between said first and second ends of said band means respectively between said central portion and said first end and between said central portion and said second end, said second width being greater than said first width, said central portion of said band means including a flexible aeration panel, a first non-stretchable panel supported on a first portion of said band means between and spaced apart from said elastic panel and said first fastening means, and a second non-stretchable panel supported on a second portion of said panel means between and spaced apart from said elastic panel and said second fastening means, said flexible aeration panel includes a first and second fiber, said first fiber being at partially elastic, said second fiber being substantially nonelastic, said first fiber enabling said flexible aeration panel to stretch in at least one direction, said second fiber inhibiting said flexible aeration panel from stretching in at least one direction.

* * * * *